United States Patent
Shaw

(10) Patent No.: US 9,808,361 B2
(45) Date of Patent: Nov. 7, 2017

(54) MEDICAL DEVICE FIXATION ANCHOR HAVING IMPROVED COMPACTION AND DELIVERY

(75) Inventor: Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1148 days.

(21) Appl. No.: 12/817,230

(22) Filed: Jun. 17, 2010

(65) Prior Publication Data

US 2010/0324584 A1 Dec. 23, 2010

Related U.S. Application Data

(60) Provisional application No. 61/187,688, filed on Jun. 17, 2009.

(51) Int. Cl.
*A61F 2/82* (2013.01)
*A61F 2/86* (2013.01)
*A61F 2/848* (2013.01)

(52) U.S. Cl.
CPC ........ *A61F 2/86* (2013.01); *A61F 2002/8483* (2013.01); *A61F 2220/0016* (2013.01)

(58) Field of Classification Search
CPC ..................................... A61F 2/06; A61F 2/82
USPC ....................................................... 623/1.36
See application file for complete search history.

(56) References Cited

U.S. PATENT DOCUMENTS

| | | | |
|---|---|---|---|
| 5,423,851 A | 6/1995 | Samuels | |
| 6,007,558 A | 12/1999 | Ravenscroft et al. | |
| 6,042,605 A | 3/2000 | Martin et al. | |
| 6,361,637 B2 | 3/2002 | Martin et al. | |
| 6,517,573 B1 | 2/2003 | Pollock et al. | |
| 6,520,986 B2 | 2/2003 | Martin et al. | |
| 2003/0220683 A1 | 11/2003 | Minasian et al. | |
| 2008/0132996 A1* | 6/2008 | Drasler | A61F 2/07 623/1.15 |
| 2009/0082847 A1 | 3/2009 | Zacharias et al. | |

FOREIGN PATENT DOCUMENTS

| | | |
|---|---|---|
| CN | 1555769 | 12/2004 |
| CN | 2887334 | 4/2007 |
| CN | 101031254 | 9/2007 |
| CN | 101234046 | 8/2008 |
| CN | 101351168 | 1/2009 |
| EP | 732088 | 9/1996 |
| EP | 1880693 | 1/2008 |
| JP | H08299456 | 3/1996 |
| JP | 2005-525910 | 9/2005 |
| WO | 01/76509 | 10/2001 |
| WO | 2005/099627 | 10/2005 |
| WO | 2005/102214 | 11/2005 |

OTHER PUBLICATIONS

International Search Report and Written Opinion, PCT/US2010/001748, dated Aug. 4, 2010, 13 pages.
International Search Report and Written Opinion, PCT/US2010/001765, dated Oct. 5, 2010, 14 pages.

* cited by examiner

*Primary Examiner* — Matthew Schall

(57) ABSTRACT

A medical fixation device having a device attachment portion, a compression bearing portion and a barb portion. The barb portion is separated from a device constraining means by the incorporation of the compression bearing portion.

20 Claims, 3 Drawing Sheets

MEDICAL DEVICE FIXATION ANCHOR HAVING IMPROVED COMPACTION AND DELIVERY

CROSS REFERENCE TO RELATED APPLICATIONS

This application claims priority to provisional application U.S. Ser. No. 61/187,688, filed Jun. 17, 2009.

BACKGROUND OF THE INVENTION

Field of the Invention

The invention relates to a medical device fixation anchor and in particular with an anchor that enhances the methods of compressing the anchor into a constraining means along with the method of releasing the constraining means.

Discussion of the Related Art

Various medical devices require some form of fixation or anchoring to a targeted site. Common anchoring means include barbs, hooks, sutures or other features used to attach a device to the surrounding anatomy. Some examples of devices requiring a means to anchor include vena-cava filters, stents, stent grafts, bile/urinary duct stents, intestinal/gastro stents and liners, occluders, electrophysiological leads, various monitors or diagnostic devices, central venous catheters and other devices as commonly know in the art. Many of these devices are pre-compacted and constrained to a small profile to allow minimally invasive delivery to an anatomical site. Once positioned at the desired site, the constraining means is removed, allowing the device to self expand and engage the surrounding anatomy.

Current anchors often interfere with the device compaction process. For example, as the device is forced into a small diameter constraining means, the sharp tip of a barb can snag or puncture the constraining means. Current anchors can also compromise the removal of a constraining means. For example, as the constraining means is being removed, a sharp anchor barb can penetrate the constraint, resulting in a delivery failure or other complication.

SUMMARY OF THE INVENTION

An embodiment of the present invention includes a medical fixation device, comprising a flexible anchor having a device attachment portion, a compression bearing portion, and a barb portion;

the device attachment portion being coupled to a medical device;

the compression bearing portion being positioned between the device attachment portion and the barb portion;

the flexible anchor having an expanded state and a compacted state;

the compacted state being maintained by a removable constraint;

while in the compacted state the compression bearing portion being in contact with the removable constraint; and while in the compacted state the barb portion being separated from the removable constraint.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, to illustrate embodiments of the invention, and together with the description serve to explain the principles of the invention.

DETAILED DESCRIPTION OF THE ILLUSTRATED EMBODIMENTS

The invention is directed to a medical device anchoring or fixation means that enhances the ease of initial compaction and subsequent device deployment.

Figure 1A:
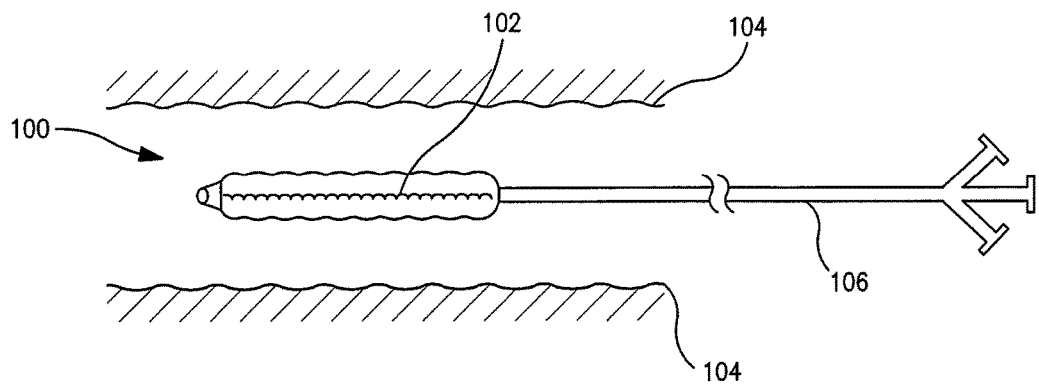
FIG. 1A is a partial side view of a medical device prior to implantation. The medical device is shown in a compacted state, the compacted state is maintained by a constraining means.
Figure 1B:
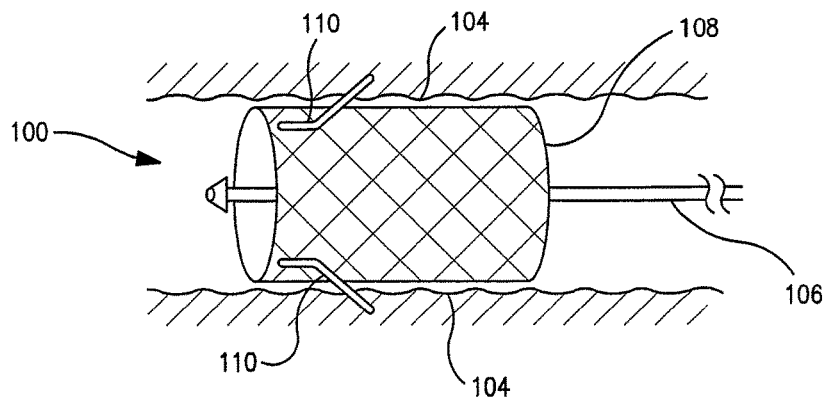
FIG. 1B is a partial side view of medical device that has self-expanded after the removal of the constraining means.

FIGS. 1A and 1B show a general example of a medical device delivery sequence. Shown in partial side view, FIG. 1A is a compacted medical device 100. The specific medical device shown is a self expanding stent graft, having a removable sheath constraining means 102. The medical device is shown positioned within a vessel 104. The constrained medical device is shown compacted onto a delivery catheter 106.

Shown in partial side view, FIG. 1B is the medical device 100 in an expanded state. Shown is a self-expanding stent graft 108, the delivery catheter 106 and two flexible anchors 110. The two flexible anchors 110 are shown at least partially penetrating the vessel 104.

Figure 2A:
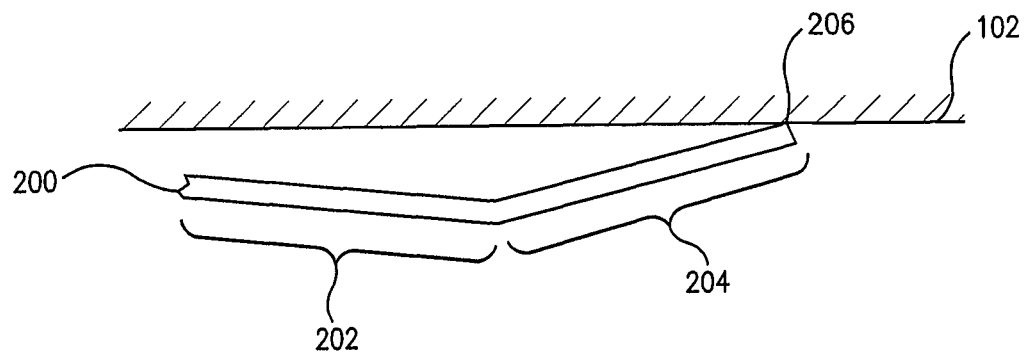
FIGS. 2A and 2B are partial side views of commonly known flexible anchors, shown in compacted and expanded states.
Figure 2B:
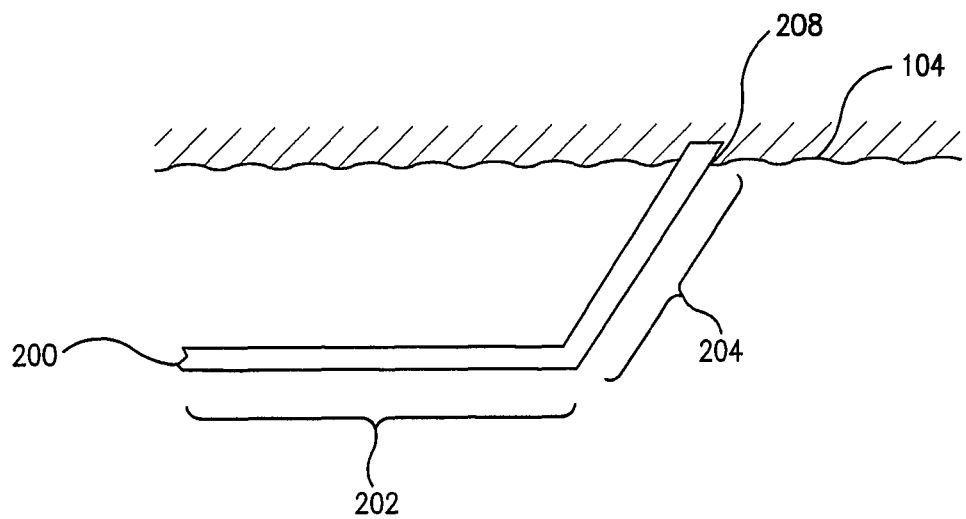

FIGS. 2A and 2B show partial side views of a typical medical device anchor. Shown in FIG. 2A is a flexible anchor 200 in a constrained or compressed state. The anchor 200 has a device attachment portion 202 useful to join the anchor to the medical device, and a barb portion 204. The flexible anchor is shown constrained by a constraining means 102. As shown in FIG. 2A, the anchor barb portion 204 is forced into contact with the constraining means 102, resulting in an interference point 206. The interference at point 206 between the sharp barb and the constraining means can allow the barb to penetrate the constraining means, or create excess friction that could compromise the removal of the constraining means 102.

As shown in FIG. 2B, the device attachment portion 202 and the barb portion 204 of the anchor have self-expanded to engage a lumen wall 104 upon removal of the constraining means. Also shown is an interference or penetration point 208 between the barb and the vessel.

Figure 3A:
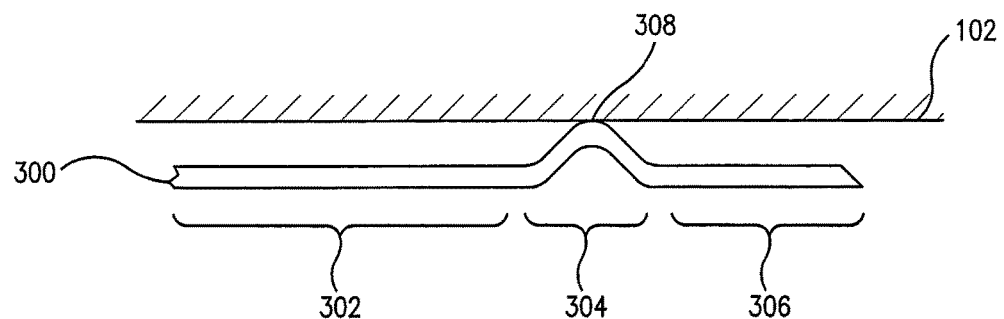
FIGS. 3A and 3B show partial side views of an improved anchor incorporating a compression bearing portion.
Figure 3B:
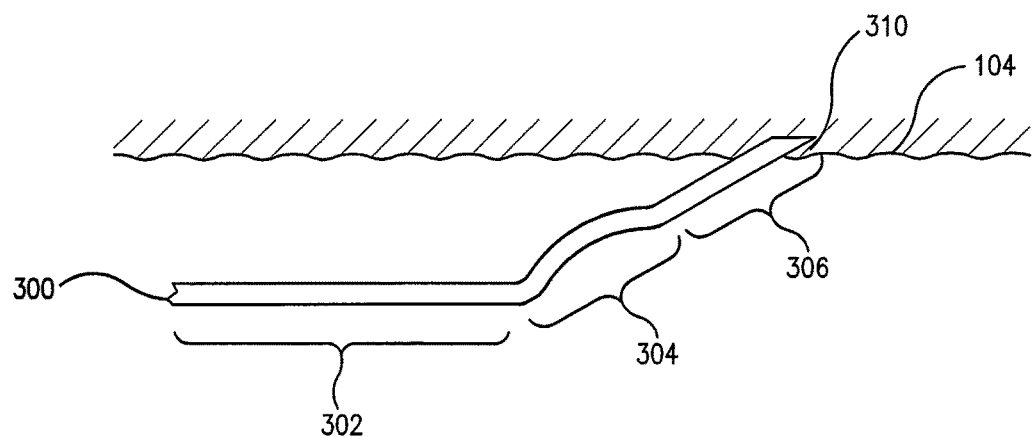

FIGS. 3A and 3B are partial side views of an improved flexible anchor. The anchor 300 has a device attachment portion 302, a compression bearing portion 304 and a barb portion 306. The barb portion may be of any desired length effective to puncture a lumen wall or other desired location for attachment of the anchor device. As shown in FIG. 3A, the flexible anchor 300 is constrained to a compacted shape by a constraining means 102. The constraining means 102 bears against the compression bearing portion 304 at contact point 308. As shown in a compacted state, the barb portion 306 is separated from the constraining means 102. The separation between the barb portion and the constraining means is caused by the shape of the compression bearing portion 304. A compression bearing portion 304 can be configured in a variety of ways and may include curved, protruding, flat or any other profile that will affect a separation between a barb and a constraining means while in a constrained state.

As shown in FIG. 3B, the device attachment portion 302, the compression bearing portion 304 and the barb portion 306 of the anchor 300 have self-expanded to engage the vessel wall 104 upon removal of the constraining means. Also shown is an interference or penetration point 310 between the barb and the vessel.

The medical device shown in FIGS. 1 through 3 is a self expanding stent graft that is held in a constrained state by a constraining sheath 102. The constraining sheath may utilize a pull cord terminating in a "rip-cord" stitch. When tensioned, the pull cord "un-stitches" to release the constraining sheath. Stent grafts and constraining sheaths can be fabricated according to the methods and materials as generally disclosed in, for example, U.S. Pat. No. 6,042,605 issued to Martin et al., U.S. Pat. No. 6,361,637 issued to Martin et al. and U.S. Pat. No. 6,520,986 issued to Martin et al.

A removable constraining means for a self-expanding medical device can include sheaths that are subsequently removed or left adjacent to the implanted device. Multiple sheaths can be used with a single or with multiple devices. Other forms of removable constraints include "pull-back" or "push-out" tubes, frangible constraints, removable constraining stitches or pins or any other suitable means as known in the art.

Depending upon the intended use, flexible anchors can comprise commonly known materials (or combinations of materials) such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), metals, nitinols, Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX), bio-absorbable materials and metals such as stainless steel, nickel/titanium alloys, and the like.

Typical methods used in the assembly of anchors to medical devices include commonly known techniques used to attach two or more components. Examples of permanent attachments include the use of glues, adhesives, welds, insert molding, heavy press-fits, one-way snap or lock features, pressed pins, heat staking, and rivets. Examples of semi-permanent attachments or those that require a tool to separate the components include screws, threaded fasteners, snap-rings, and snap-fits. Examples of releasable attachments or those that can be separated by hand without the use of an additional tool include snap-fits, twist lock features, push to release features, squeeze to release features, slide levers, latches, and light press-fits.

Anchors can have various cross-sectional profiles such as circular, oval, rectangular or other polygon shapes. Anchors can also incorporate external lubricious layers, lubricious coatings, or lubricious wrappings to minimize friction. Anchors can also incorporate therapeutic agents tailored for specific biological results. Anchors can also include radiopaque markers or radiopaque intensifiers.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A medical device including an anchor having an expanded state and a constrained state, the anchor comprising:
a device attachment portion for coupling to a medical device,
a barb portion, and
a compression bearing portion positioned between the device attachment portion and the barb portion,
wherein in the constrained state, the compression bearing portion adopts a first non-linear configuration and effects a separation between the barb portion and a constraining member, and
wherein in the expanded state, the compression bearing portion adopts a second non-linear configuration and the barb portion is adapted to penetrate a vessel wall.

2. The medical device of claim 1, wherein the barb portion is metal.

3. The medical device of claim 1, further comprising:
a constraining member,
wherein the device attachment portion is coupled to the medical device,
and wherein the constraining member operates to maintain the anchor in the constrained state such that the compression bearing portion is in contact with the constraining member.

4. A medical device including an anchor having an expanded state and a constrained state, the anchor comprising:
a device attachment portion for coupling to a medical device,
a barb portion, and
a compression bearing portion positioned between the device attachment portion and the barb portion, wherein in the constrained state, the compression bearing portion is curved relative to the barb portion and effects a separation between the barb portion and a constraining member, and wherein in the expanded state, the compression bearing portion is curved relative to the barb portion and the barb portion is adapted to penetrate a vessel.

5. The medical device of claim 4, wherein a curvature of the compression bearing portion in the constrained state is different than a curvature of the compression bearing portion in the expanded state.

6. A medical device including an anchor having an expanded state and a constrained state, the anchor comprising:
- a device attachment portion for coupling to a medical device, the device attachment portion having a length and a first longitudinal axis extending along the length of the device attachment portion,
- a barb portion having a length and a second longitudinal axis extending along the length of the barb portion, and
- a compression bearing portion positioned between the device attachment portion and the barb portion,
- wherein in the constrained state, the compression bearing portion has a first apex that is offset relative to the second longitudinal axis and effects a separation between the barb portion and a constraining member, and
- wherein in the expanded state, the compression bearing portion has a second apex that is offset relative to the second longitudinal axis and the barb portion is adapted to penetrate a vessel.

7. The medical device of claim 6, wherein in the constrained state, the compression bearing portion has a first curvature including the first apex, and wherein in the expanded state the compression bearing portion has a second curvature including the second apex.

8. The medical device of claim 7, wherein the first and second curvatures are different.

9. The medical device of claim 6, wherein in at least one of the constrained state and the expanded state the compression bearing portion includes a curved portion.

10. The medical device of claim 6, wherein in both the constrained state and the expanded state the compression bearing portion includes at least one of a curved portion or a flat portion.

11. The medical device of claim 6, wherein in at least one of the constrained state and the expanded state the compression bearing portion includes a flat portion.

12. The medical device of claim 6, further comprising a hinge point situated between the device attachment portion and the compression bearing portion, wherein in transitioning between the constrained state and the expanded state, the compression bearing portion and the barb portion pivot about the hinge point.

13. The medical device of claim 12, wherein the second longitudinal axis pivots about the hinge point.

14. The medical device of claim 6, wherein in the expanded state, the first and second longitudinal axes are angularly offset relative to one another.

15. A medical device including an anchor having an expanded state and a constrained state, the anchor comprising:
- a device attachment portion for coupling to a medical device, the device attachment portion having a length and a first longitudinal axis extending along the length of the device attachment portion,
- a barb portion having a length and a second longitudinal axis extending along the length of the barb portion, and
- a compression bearing portion positioned between the device attachment portion and the barb portion,
- wherein in the constrained state, the compression bearing portion protrudes away from the second longitudinal axis and effects a separation between the barb portion and a constraining member, and
- wherein in the expanded state, the compression bearing portion protrudes away from the second longitudinal axis and the barb portion is adapted to penetrate a vessel.

16. The anchor of claim 15, wherein the barb portion and the device attachment portion remain free from contacting each other in both the constrained state and the expanded state.

17. The medical device of claim 15, wherein in at least one of the constrained state and the expanded state the compression bearing portion includes a curved portion.

18. The medical device of claim 15, wherein in at least one of the constrained state and the expanded state the compression bearing portion includes a flat portion.

19. The medical device of claim 15, wherein in both the constrained state and the expanded state the compression bearing portion includes at least one of a curved portion or a flat portion.

20. The medical device of claim 15, wherein in the expanded state, the first and second longitudinal axes are angularly offset relative to one another.

* * * * *